(12) United States Patent
Perot et al.

(10) Patent No.: US 9,333,146 B2
(45) Date of Patent: May 10, 2016

(54) COMPACT INJECTION DEVICE

(75) Inventors: Frédéric Perot, Saint Paul de Varces (FR); Franck Carrel, Pont de Claix (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 189 days.

(21) Appl. No.: 13/990,646

(22) PCT Filed: Dec. 14, 2010

(86) PCT No.: PCT/IB2010/003491
§ 371 (c)(1),
(2), (4) Date: May 30, 2013

(87) PCT Pub. No.: WO2012/080776
PCT Pub. Date: Jun. 21, 2012

(65) Prior Publication Data
US 2013/0256166 A1    Oct. 3, 2013

(51) Int. Cl.
| *A61M 5/32* | (2006.01) |
| *A61J 1/00* | (2006.01) |
| *A61M 5/00* | (2006.01) |
| *A61M 5/31* | (2006.01) |
| *A61M 5/315* | (2006.01) |

(52) U.S. Cl.
CPC . *A61J 1/00* (2013.01); *A61M 5/002* (2013.01); *A61M 5/315* (2013.01); *A61M 5/3129* (2013.01); *A61M 5/31511* (2013.01); *A61M 2005/31518* (2013.01)

(58) Field of Classification Search
CPC ............. A61M 5/002; A61M 5/3129; A61M 5/31511; A61M 5/315; A61M 31/00; A61M 3/0262; A61J 1/00
USPC .......... 206/365, 226, 395; 604/194, 234, 184, 604/193, 219, 226
See application file for complete search history.

(56) References Cited

U.S. PATENT DOCUMENTS

| 3,783,997 | A | * | 1/1974 | Brown | ........................... 206/365 |
| 3,820,652 | A | * | 6/1974 | Thackston | ..................... 206/365 |
| 3,916,893 | A | * | 11/1975 | De Felice | ...................... 604/193 |
| 4,011,868 | A | | 3/1977 | Friend | |
| 4,581,023 | A | * | 4/1986 | Kuntz | ........................... 604/234 |
| 5,324,274 | A | * | 6/1994 | Martin | ........................... 604/248 |
| 8,517,996 | B2 | | 8/2013 | Fontana | |

FOREIGN PATENT DOCUMENTS

| WO | 9729798 A1 | | 8/1997 | |
| WO | 2010034462 A1 | | 4/2010 | |
| WO | 2010089653 A1 | | 8/2010 | |
| WO | WO2010089653 | * | 8/2010 | ............ A61M 31/00 |

* cited by examiner

*Primary Examiner* — Chun Cheung
(74) *Attorney, Agent, or Firm* — The Webb Law Firm

(57) ABSTRACT

A package for a container including a tubular barrel having open distal and proximal ends, the proximal end being sized and shaped to receive a plunger, and the distal end being sized and shaped to receive an injection needle, the package including a plunger rod for the container, a part of the plunger rod being shaped complementarily to at least a part of the external shape of the tubular barrel, and a tray connectable to the plunger rod, the tray and the plunger rod forming the package when they are connected to each other.

18 Claims, 12 Drawing Sheets

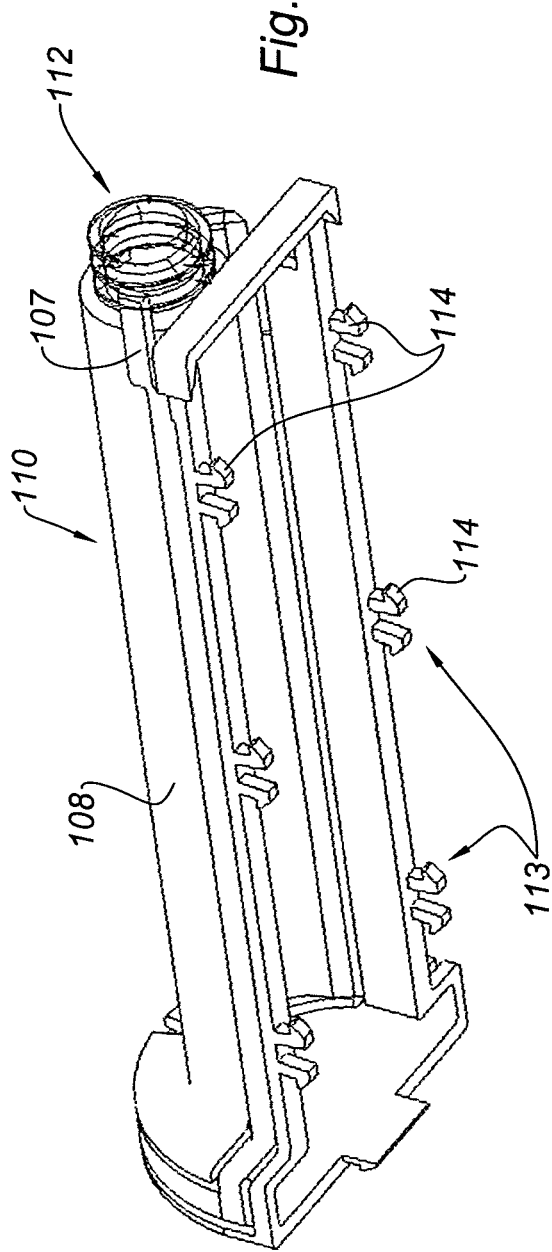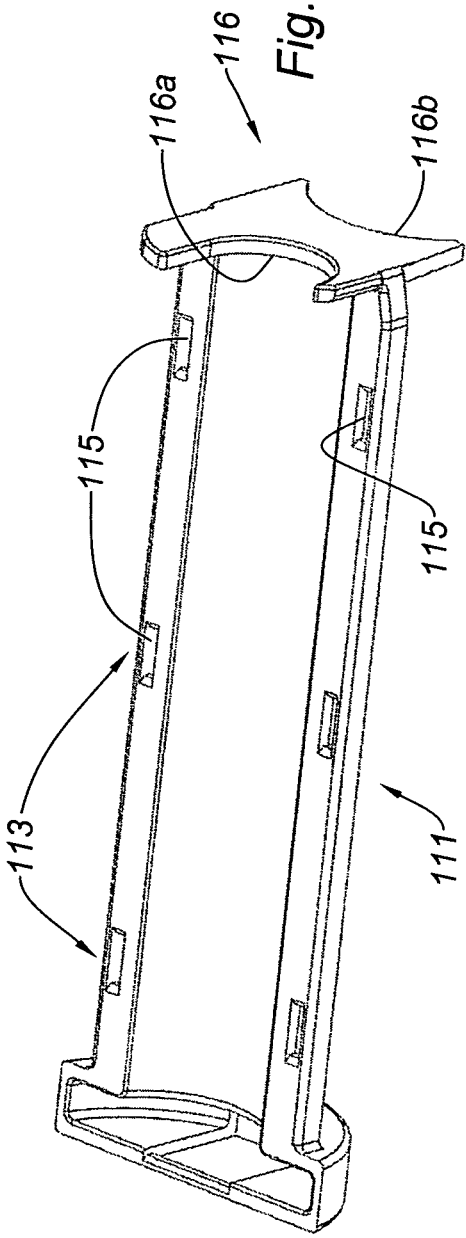

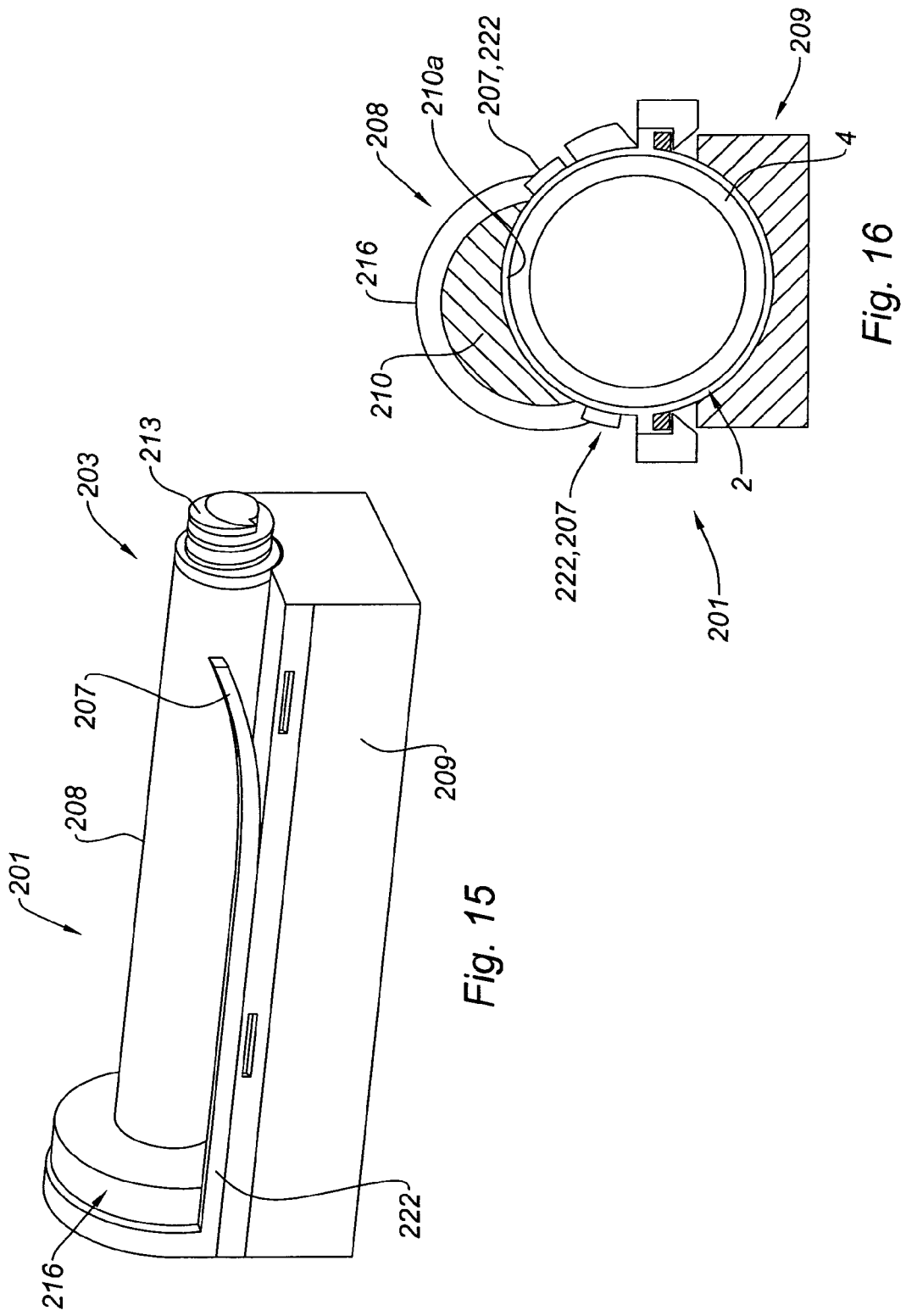

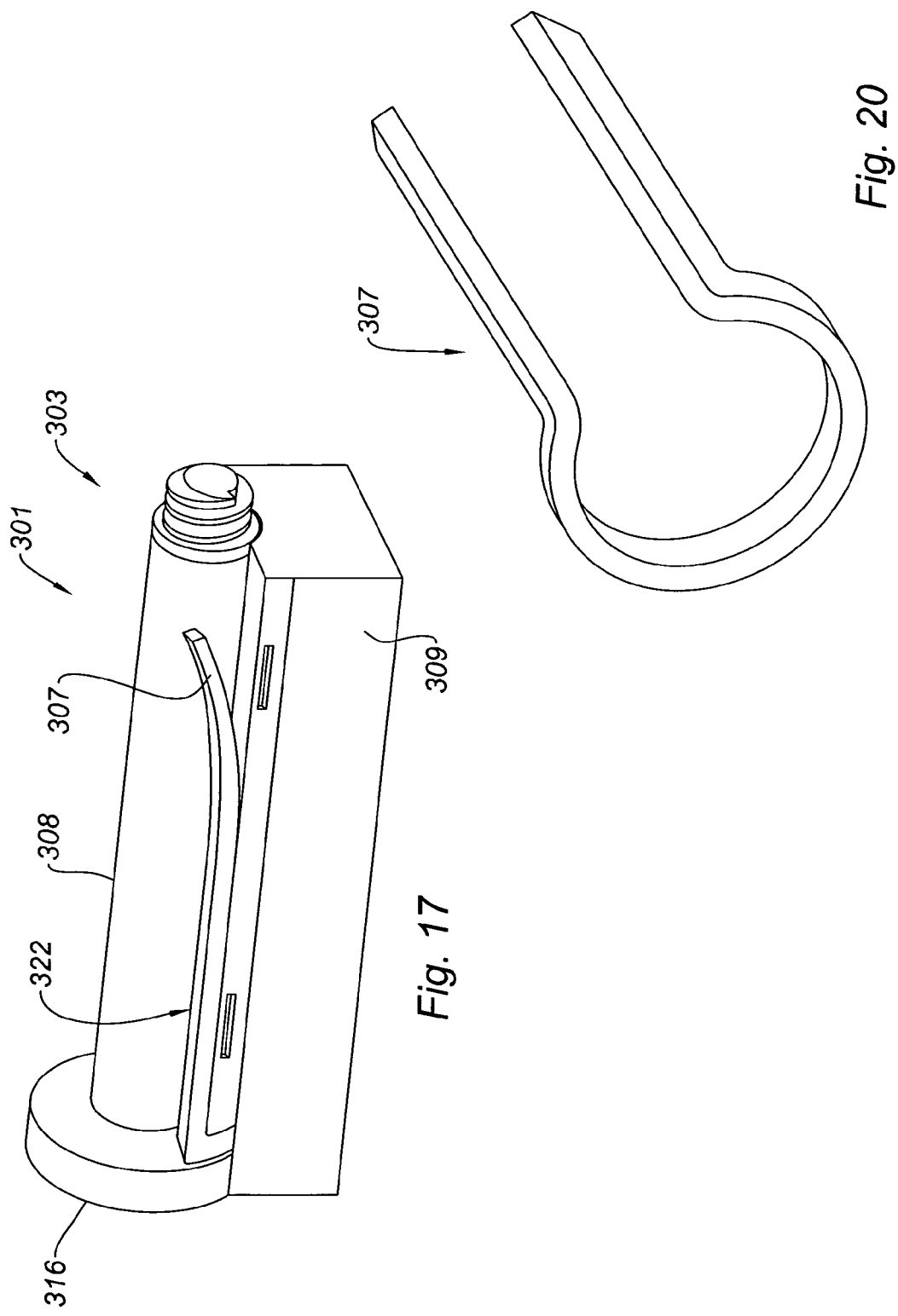

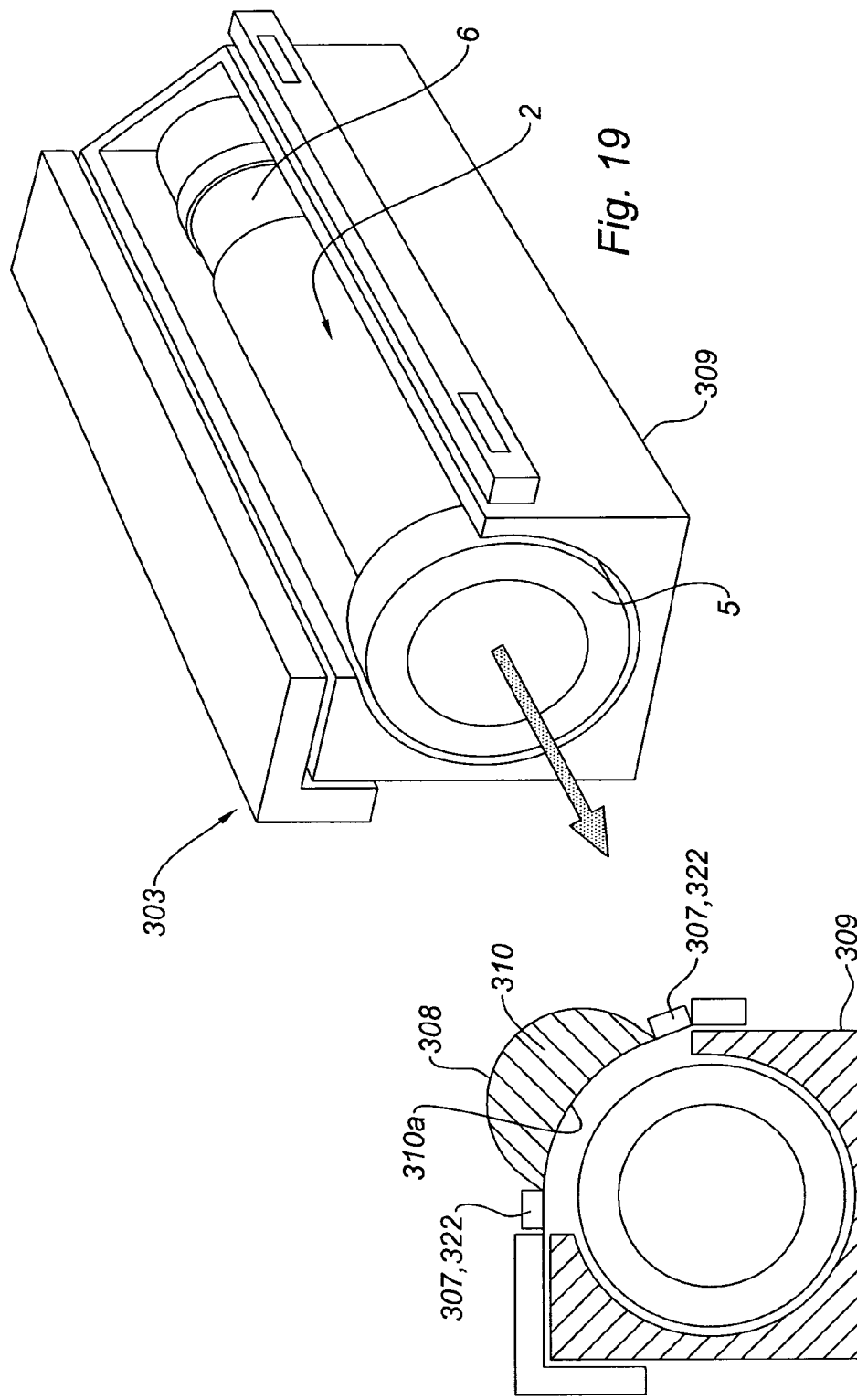

COMPACT INJECTION DEVICE

Figure 1:
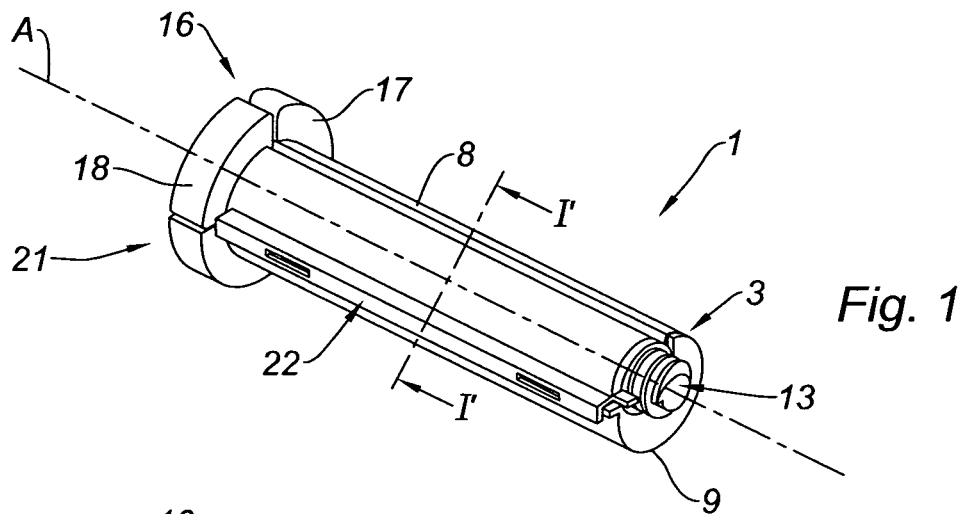

The present invention relates to a package for a container and to a drug delivery device obtained from the packaged container.

In this application, the distal end of a component or of a device means the end furthest away from the hand of the user and the proximal end means the end closest to the hand of the user, when the component or device is in the in-use position. Similarly, in this application, the terms "in the distal direction" and "distally" mean in the direction of the injection or of the delivery of the product, and the terms "in the proximal direction" and "proximally" mean in the direction opposite to the direction of injection.

Injection devices or drug delivery devices, such as syringes, are well known. Many different types of injection devices have been designed for administering medicines. Injection or drug delivery devices usually comprise a container intended to receive the product to be injected and a plunger rod intended to move the plunger within the container so as to expel the product therefrom at the time of injection. Such injection devices may be Luer syringes or staked needle syringes. In particular, prefilled disposable injection devices are now preferred because they are convenient, safe and efficient and may be used directly in emergency cases.

Prefilled injections devices are filled by a pharmaceutical company, packaged for use, and then typically stored at a doctor's office, hospital, etc. until it is needed for use. In such a condition, the prefilled injection device will take up a predetermined amount of storage space based upon the size of the injection device (typically comprised of a syringe barrel, a plunger, a plunger rod, and possibly a needle). In some cases, the predetermined amount of storage space the injection device will take up is a maximum space approximating the length of the plunger rod, plus the length of the syringe barrel, plus the length of the needle (if provided).

Required storage space is an important feature of prefilled injection devices. It is especially important in the case of prefilled injection devices, when the medicine they contain must be stored and transported at low temperatures. Storage of these injection devices requires refrigeration and may be expensive. This is especially the case in hospitals and pharmacies, where storage space for medicines is limited.

Thus, there is a need for a drug delivery device which would be particularly compact when in its storage condition, particularly when the device is prefilled. There is a need for drug delivery device that can be packaged in a very compact way.

Solutions of the prior art have consisted in providing the plunger rod separated from the container, or in providing the plunger rod with a hinge so as to fold it along the container, thereby reducing the overall length of the device to be packaged, as described in U.S. Pat. No. 4,011,868.

Nevertheless, the drug delivery devices of the prior art still occupy a large volume, at least in width but also in length depending on the shape of the plunger rod, and present a less desirable solution, because their outer shape is not symmetrical.

There is therefore the need for a compact drug delivery device having an outer shape occupying the smallest volume possible in the storage condition of the device and being easy to store with other devices having the same volume/shape, so that as little space as possible is wasted when a large number of these devices is stored, for example in an inventory of a hospital or a pharmacy.

Moreover, such a drug delivery device must be simple to use, and preferably would not alter the typical process followed by a caregiver when administering an injection.

An aspect of the present invention is therefore to provide a package for the container of a drug delivery device, said package allowing the overall length of the combination of the container and the plunger rod to be reduced in the packaged condition for storage of the drug delivery device, even in the case where the container of the drug delivery device is prefilled with a medicine.

A first aspect of the present invention relates to a package for a container comprising a tubular barrel having open distal and proximal ends, the proximal end being sized and shaped to receive a plunger, and the distal end being sized and shaped to receive an injection needle, said package comprising i) a plunger rod for said container, a part of said plunger rod being shaped complementarily to at least a part of the external shape of said tubular barrel, and ii) a tray connectable to said plunger rod, said tray and said plunger rod forming said package when they are connected to each other.

Another aspect of the invention is a plunger rod for a syringe comprising a tubular barrel having open distal and proximal ends, the proximal end being sized and shaped to receive a plunger, and the distal end being sized and shaped to receive an injection needle, a part of said plunger rod being shaped complementarily to at least a part of the external shape of the syringe barrel, said plunger rod being releasably connectable with a tray that, when connected with said plunger rod, forms a package for the syringe.

As it will appear from the description below, the package of the invention and the container packaged therein form a compact article allowing reconstituting a drug delivery device. The tray and the plunger rod are connectable so as to form a package surrounding the container. In the packaged condition of the container, the part of the plunger rod which is shaped complementarily to at least a part of the external shape of said tubular barrel is in a nesting relationship with said part of the external shape of the tubular barrel, and the plunger rod and the tray are connected to each other : as such, the volume occupied by the container and the plunger rod is reduced compared to the devices of the prior art where the plunger rod is not in a nesting relationship with a part of the external wall of the tubular barrel of the container; for example, usually in the prior art, the plunger rod is in alignment with the container. Moreover, the tray is generally designed and shaped so as to be able to receive the part of the container that is not facing the plunger rod in the packaged condition of the container: as such, the inner shape of the tray is generally concave so as to receive the container. Preferably, in general, the outer shape of the tray of the package of the invention is such that the tray is easily stackable with another same shaped tray.

In embodiments, the plunger rod and the tray are connected to each other by releasable connecting means.

Indeed, thanks to the releasable connecting means of the package of the invention, the plunger rod can be detached and separated easily from the rest of the package, i.e. from the tray, and is ready to be used. As will appear from the description below, the plunger rod may be used directly in combination with a plunger lodged within the tubular barrel in the proximal region of said tubular barrel, the tubular barrel being for example filled with a medicine to be injected.

In embodiments, at least part of said releasable connecting means is provided between said plunger rod and said tray. For example, particularly in embodiments where the plunger rod and the tray are manufactured by a co-injection moulding process, part of the releasable connecting means may be a tear-off line provided between at least a part of the plunger rod and a part of the tray. Alternatively or in combination, part of the releasable connecting means may be breakable bridges provided between the plunger rod and the tray. The tear-off line and/or the breakable bridges may be present only on a part of the junction outline between the plunger rod and the tray.

In an embodiment, the tear-off line runs all the way along the junction outline between the plunger rod and the tray. In such an embodiment, the releasable connecting means consists in one removable tear-off line delimiting the outline of said plunger rod with respect to said tray.

Alternatively or in combination, at least part of said releasable connecting means is provided on said plunger rod and on said tray. For example, the releasable connecting means comprise at least snap-fit means. In the present application, by "snap-fit means" is meant releasable snap-fit means. In such a case, usually, a member of the snap-fit means is provided on the tray and a complementary member of the snap-fit means is located on the plunger rod, said member and complementary member cooperating together so as to connect the tray to the plunger rod in a releasable way: for example, the member and the complementary member being engaged one into the other when the tray is connected to the plunger rod, a user may simply disengage one member from the complementary member, for instance by a pressure exerted on one member, so as to release the snap-fit means and disconnect the plunger rod from the tray.

Alternatively or in combination, the releasable connecting means may comprise adhesive, part of the adhesive being provided on the tray and other part of the adhesive being provided on the plunger rod, a user being able to disconnect the tray from the plunger rod by pulling the plunger rod away from the tray.

Alternatively or in combination, at least part of said releasable connecting means is provided on one of said plunger rod and tray. For example, only the tray may be provided with adhesive. Alternatively, only the plunger rod may be provided with adhesive.

In embodiments, the releasable connecting means may be any combination of the various means described above, i.e., removable tear-off lines, breakable bridges, snap-fit means, adhesives.

In embodiments, the releasable connecting means comprises at least one of a removable tear-off line and a breakable bridge: such embodiments allow the user to know whether the package has already been opened before use, as the removed tear-off line and/or the broken bridge constitute evidence of a prior opening of the package.

In embodiments, the part of the plunger rod that is shaped complementarily to at least a part of the external shape of the tubular barrel is the longitudinal section of a tube comprising a first longitudinal portion and a second longitudinal portion coupled to each other by a longitudinal living hinge. In particular, in such an embodiment, the concave side of the longitudinal section of a tube faces the external wall of the tubular barrel in the packaged condition of the container. Such a shape of the plunger rod allows therefore the plunger rod to be in a nesting relationship with the external wall of the tubular barrel, so that the plunger rod and the tubular barrel occupy as little space as possible in the packaged condition of the container. Moreover, once the plunger rod is separated from the tray, the living hinge allows the first longitudinal portion of the plunger rod to be folded on the second longitudinal portion of the plunger rod thereby reconstituting a rigid rod out of said two longitudinal portions, said rigid rod being capable of being received within the tubular barrel so as to perform efficiently its function as a plunger rod for moving the plunger within the tubular barrel. The rigidity of the plunger rod is therefore reinforced by the presence of the double wall formed by the first and second longitudinal portions.

In embodiments, the two longitudinal portions further include clipping means so that they may be clipped one on to the other and be maintained locked in their folded position. The reconstituted plunger rod is therefore made reliable and may not deviate or collapse during use.

In such embodiments, part of the releasable connecting means for connecting the plunger rod to the tray may be used as the clipping means for maintaining the first and the second longitudinal portions of the plunger rod folded one on to the other. For example, in embodiments where at least part of the releasable connecting means are snap-fit means, at least a first member of said snap-fit means being located on said first longitudinal portion and a second member of said snap-fit means being located on said second longitudinal portion, said first and second members are engageable with each other when said plunger rod is not connected to the tray, so as to maintain said first longitudinal portion folded on said second longitudinal portion. The rigidity of the plunger rod is therefore reinforced by the fact that the double wall formed by the first and second longitudinal portions folded on each other is locked by said first and second members.

In embodiments, the part of the plunger rod that is shaped complementarily to at least a part of the external shape of the tubular barrel is a solid shaft showing at least one concave longitudinal face.

Such a shape of the plunger rod allows the plunger rod to be in a nesting relationship with the external wall of the tubular barrel, so that the plunger rod and the barrel occupy as little space as possible in the packaged condition of the container: indeed in such a condition of the container, the concave longitudinal face of the shaft faces the external wall of the tubular barrel. Moreover, once the plunger rod is separated from the tray, the plunger rod is readily usable safely and efficiently, since the shaft it is made of is solid and has the required rigidity for its function. The solid shaft may be formed of a material selected from polyolefin materials such as polyethylene or polypropylene.

In embodiments, the package further comprises attaching means for attaching said plunger rod with the plunger intended to be received in said container. For example, the attaching means is provided at a distal end of one of said first longitudinal portion and second longitudinal portion as described above. Alternatively, the attaching means may be provided at the distal end of the solid shaft as described above.

For example, the attaching means is a screw, and the plunger to be connected thereon has a threaded recess able to receive and cooperate with said screw. The plunger rod may then be connected to the plunger and may be used to push the plunger distally within the tubular barrel so as to expel a product to be delivered. Alternatively, the attaching means may be snap-fit means and the plunger is provided with complementary snap-fit means. In embodiments, the distal end of the plunger rod has no attaching means and the plunger rod may be used to push on the plunger by simple contact with said plunger in the distal direction.

In embodiments, a flange is provided at a proximal end of said plunger rod. The flange may provide for a pushing surface when the user has separated the plunger rod from the rest of the package and uses it to move the plunger within the tubular barrel.

Another aspect of the invention is a drug delivery device comprising:

a container for a product, said container comprising a tubular barrel having open distal and proximal ends, the proximal end being sized and shaped to receive a plunger, and the distal end being sized and shaped to receive an injection needle, and a package for said container, as described above.

Another aspect of the invention is a drug delivery device comprising:

a container for a medicament, said container comprising a tubular barrel having open distal and proximal ends, the proximal end being sized and shaped to receive a plunger, and the distal end being sized and shaped to receive an injection needle;

a plunger rod having a part shaped complementarily to at least a part of the external shape of the tubular barrel; and a tray sized and shaped complementarily to at least a part of the external size and shape of the tubular barrel, said plunger rod being releasably connectable with said tray to form a package for the container.

In embodiments, the container is prefilled with a product to be delivered. In such a case, the tubular barrel is closed at its distal end with a cap and at its proximal end by the plunger. The distal end of the tubular barrel may be provided with a needle, for example a staked needle, in which case the cap surrounds the needle so as to protect it.

When the user wishes to perform the delivery of the product contained in the packaged drug delivery device, he releases the releasable connecting means in order to open the package. For example, in embodiments where a tear-off line is a part of the releasable connecting means as described above, the user may first remove the tear-off line and then release the other releasable connecting means. Alternatively, in embodiments where the tear-off line forms the entire outline between the plunger rod and the tray, the user directly separates the plunger rod from the package by tearing off the whole length of the tear-off line and he gains access to the prefilled container by removing the tray. The user then just needs to remove the cap from the distal end of the container so as to render the needle visible and operable. In embodiments where no needle is already present at the distal end of the tubular barrel, the user may connect an adequate needle thereon. In embodiments where the plunger rod includes a solid shaft as described above, the user then may introduce the distal end of said solid shaft within the tubular barrel in order to either bring said distal end in contact with the plunger or connect it thereon, for example by screwing said distal end to the plunger, and the drug delivery device is then ready for use. In embodiments where the proximal end of the plunger rod is provided with a flange, the user may simply exert a distal pressure on this flange so as to move distally the plunger within the tubular barrel and complete delivery of the product.

In embodiments where the plunger rod is the longitudinal section of a tube with a hinge and clipping means as described above, then the user may simply fold one longitudinal portion onto the other and clip the two portions together to obtain a rigid rod usable as the plunger rod. He then may introduce the distal end of the plunger rod within the tubular barrel in order to perform the delivery of the product as described above.

In embodiments, the tray may further comprise means for stacking engagement with another said tray.

For example, the tray comprising at least a semi-tubular part, said semi-tubular part is provided with an outer transversal wall having a semi-circular concave shape complementary to the outer circular convex shape of said semi-tubular part. Such an embodiment allows the stacking up of at least two packaged drug delivery devices of the invention which can be coupled or clipped together by means of the semi-tubular part of the package of one packaged drug delivery device being engaged into the semi-circular concave shape of the other packaged drug delivery device. This allows storing two packaged drug delivery devices of the invention in a restricted volume. It is then possible to store a large number of packaged drug delivery devices of the invention in a limited space.

For example, in embodiments, the package is made of a first rigid semi-tubular shell including said plunger rod, and a second rigid semi-tubular shell, complementary to said first shell, said first and second shell being clipped together so as to form said package, said second shell being provided with said outer transversal wall.

Figure 2:
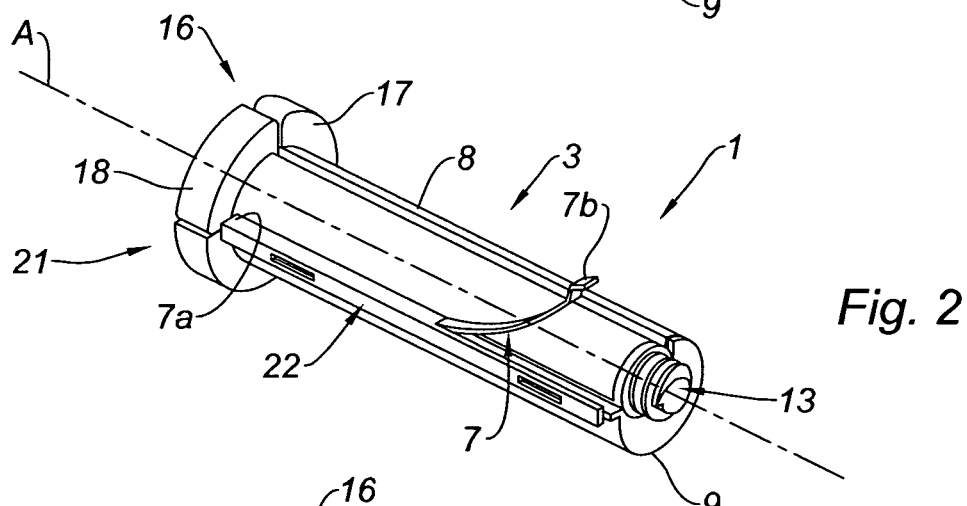
Figure 3:
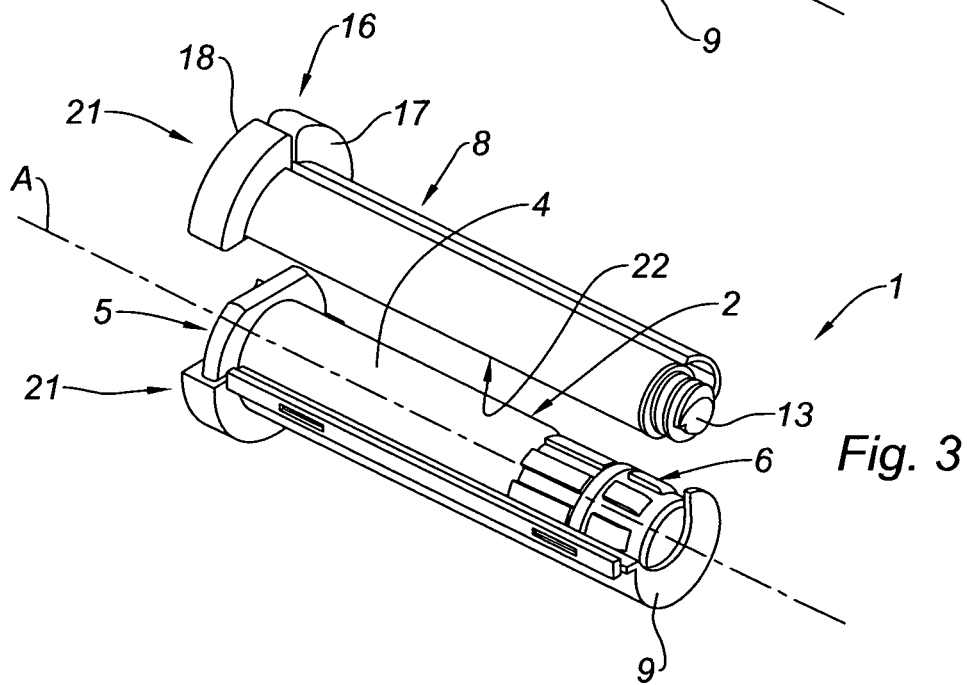
Figure 4:
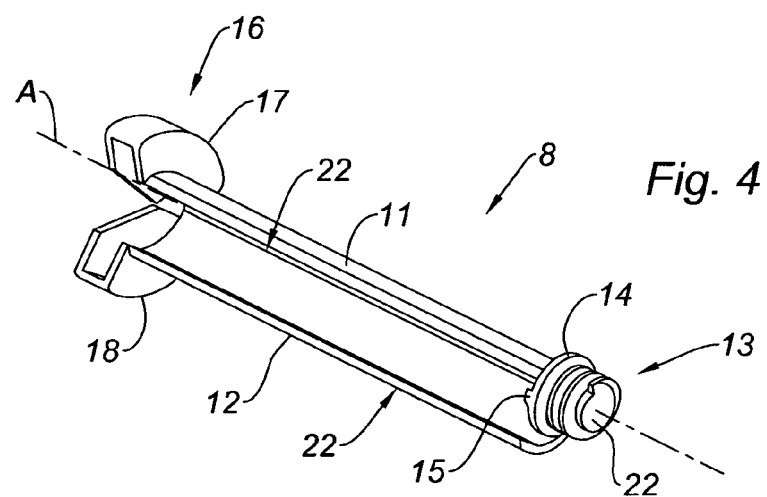
Figure 5:
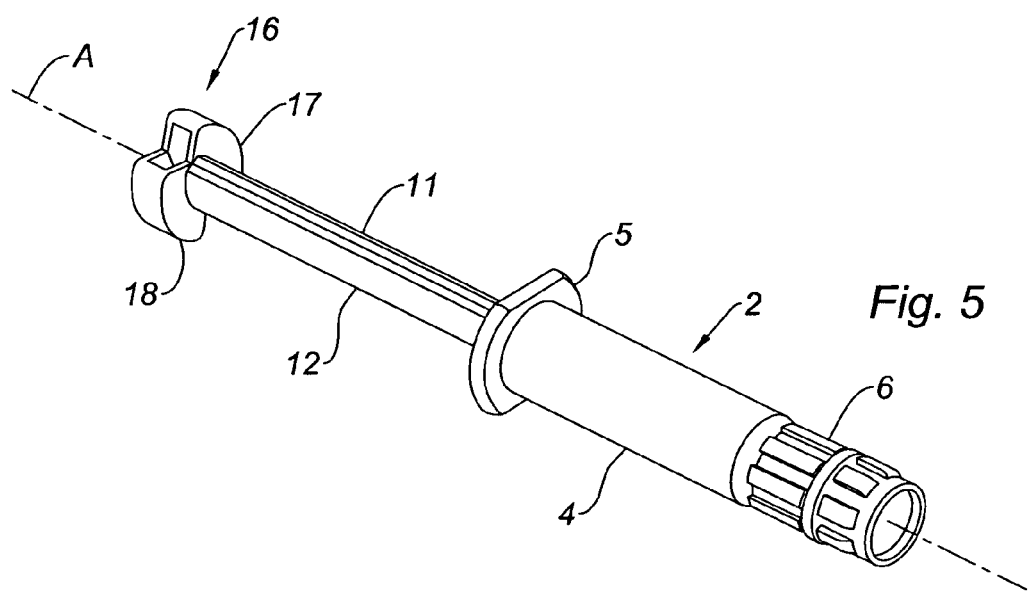
Figure 6:
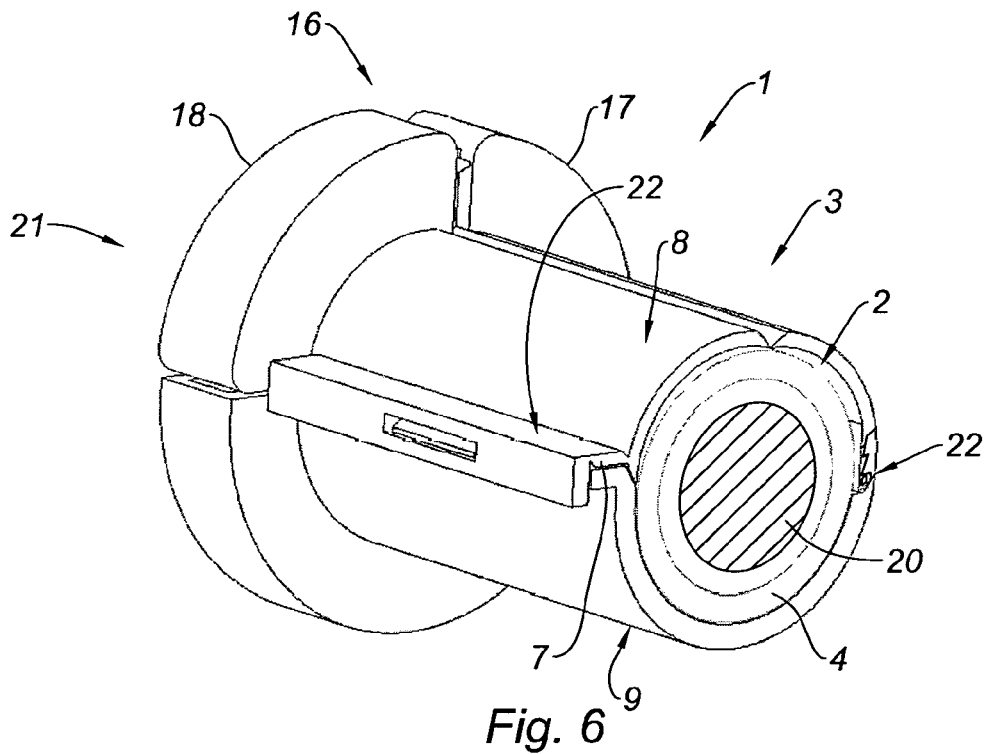
Figure 7:
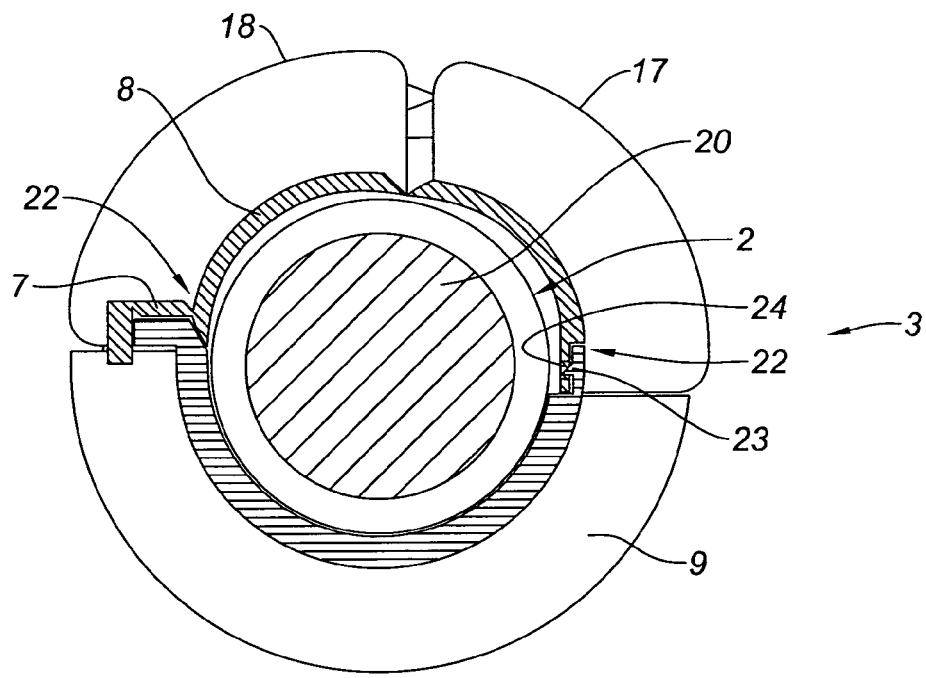
Figure 8:
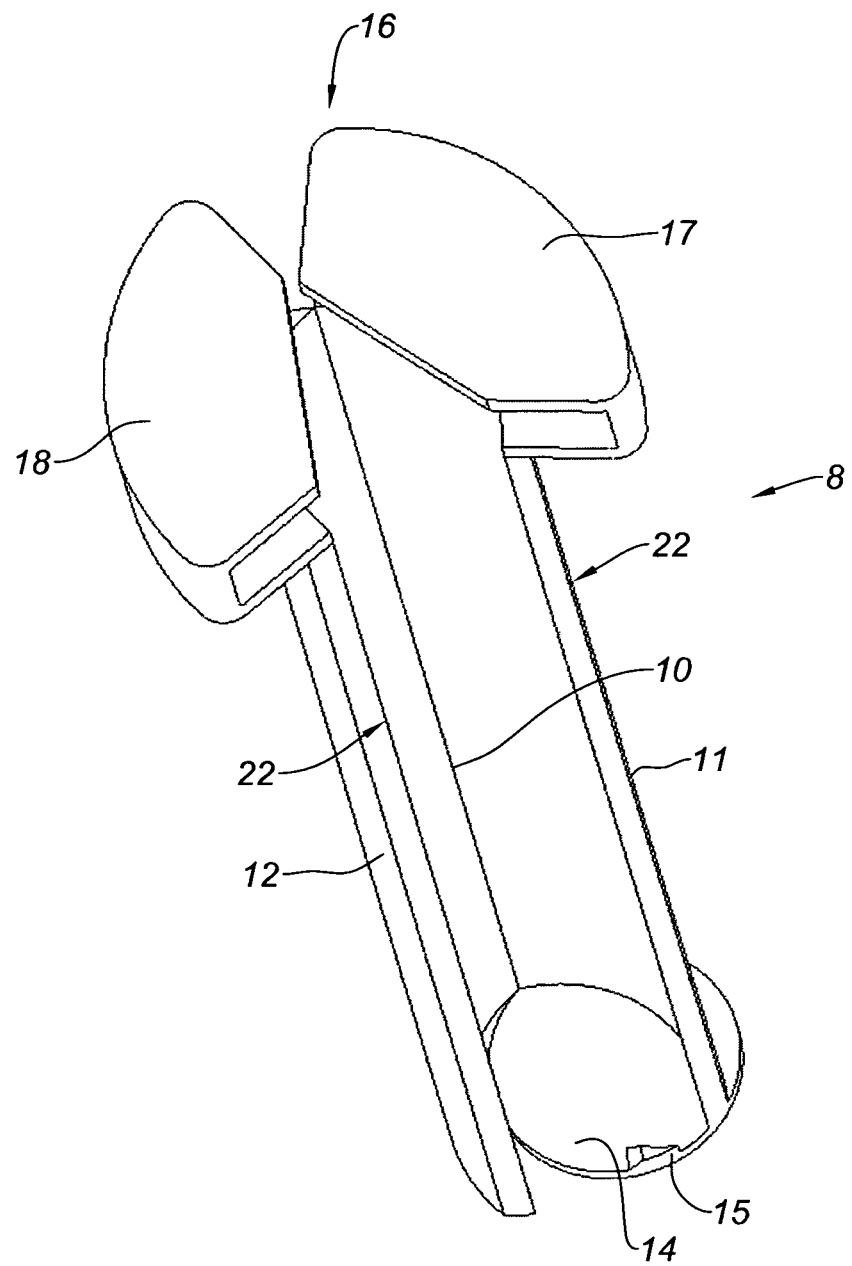
Figure 9:
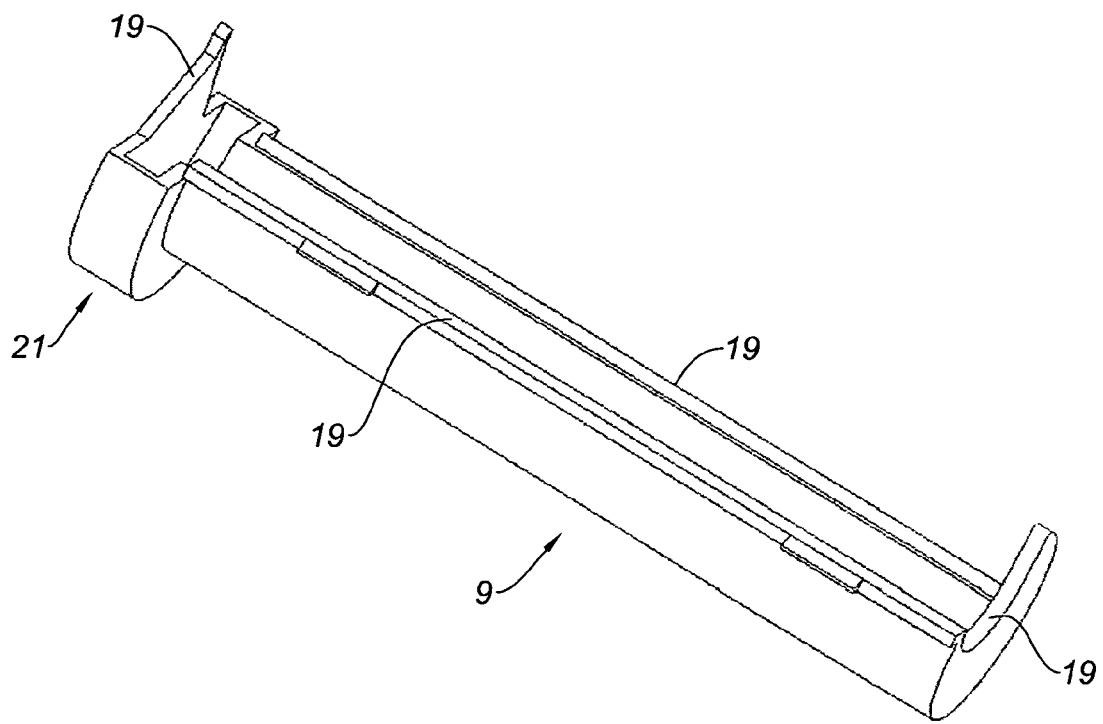
Figure 10:
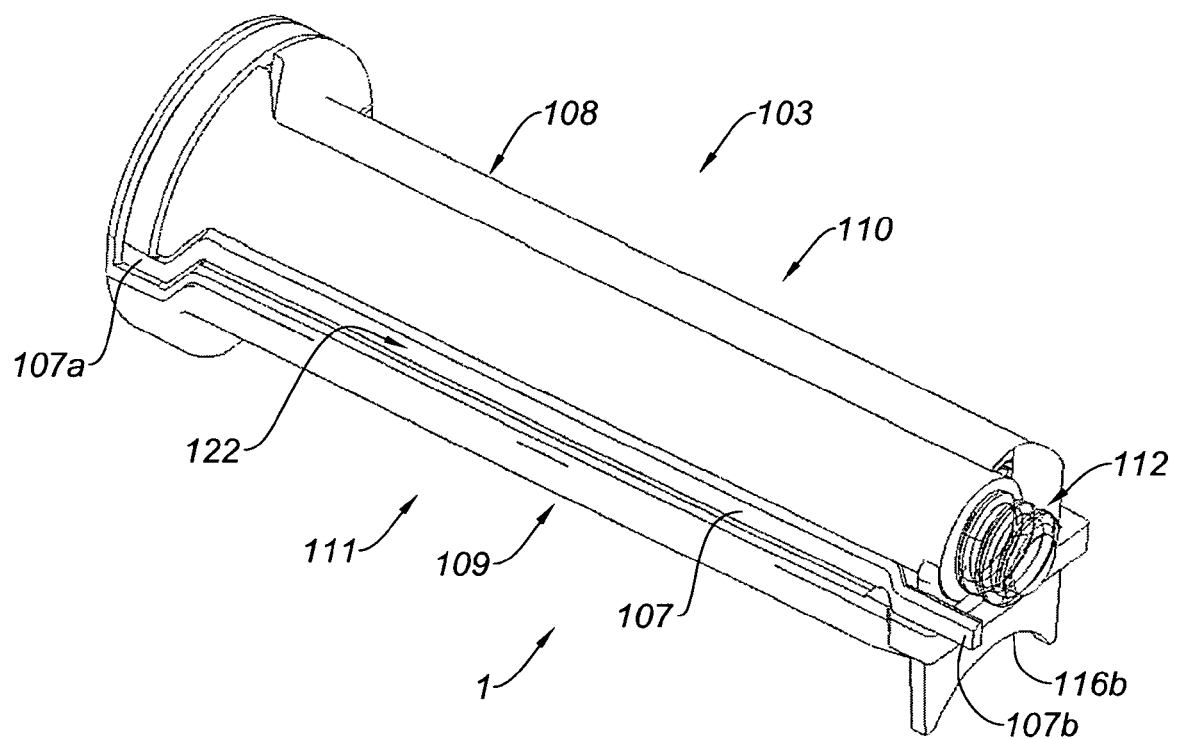
Figure 13:
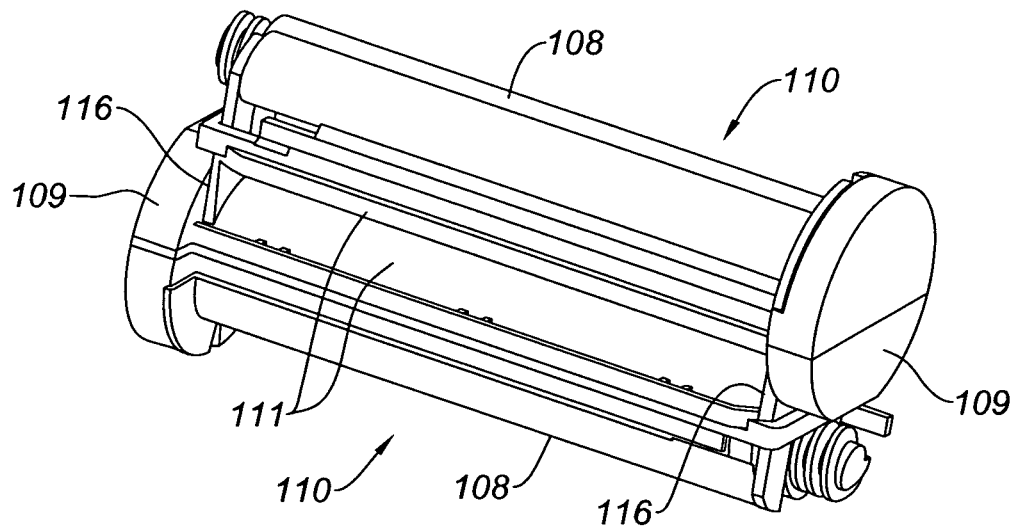
Figure 14:
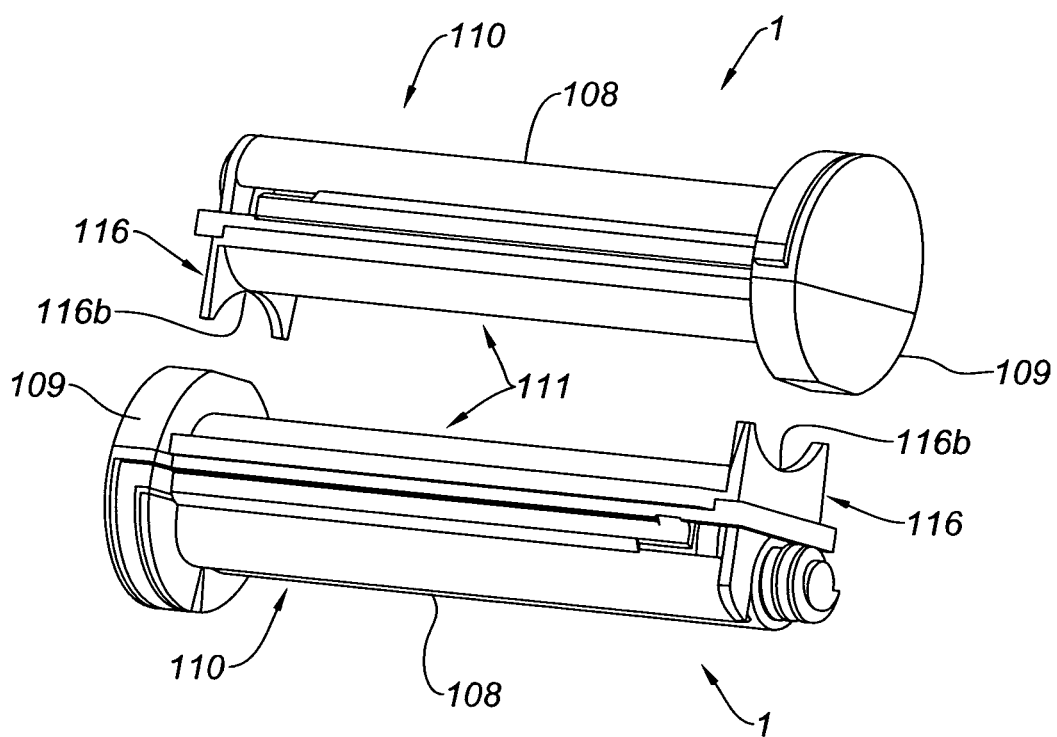
Figure 21:
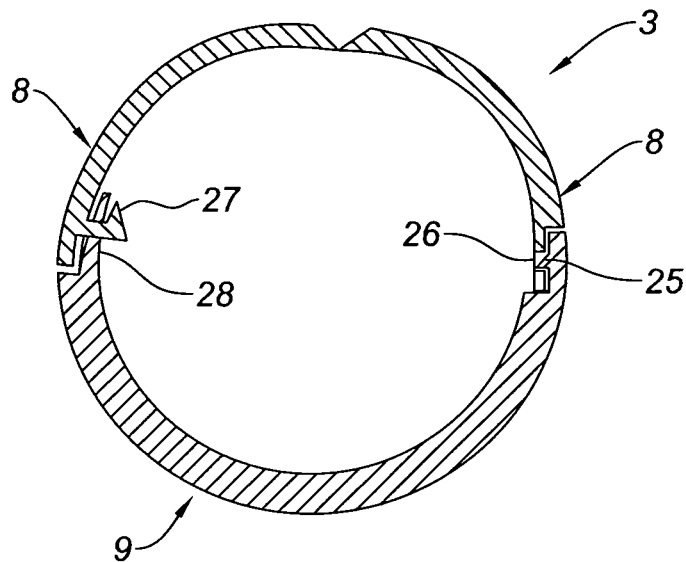
Figure 22:
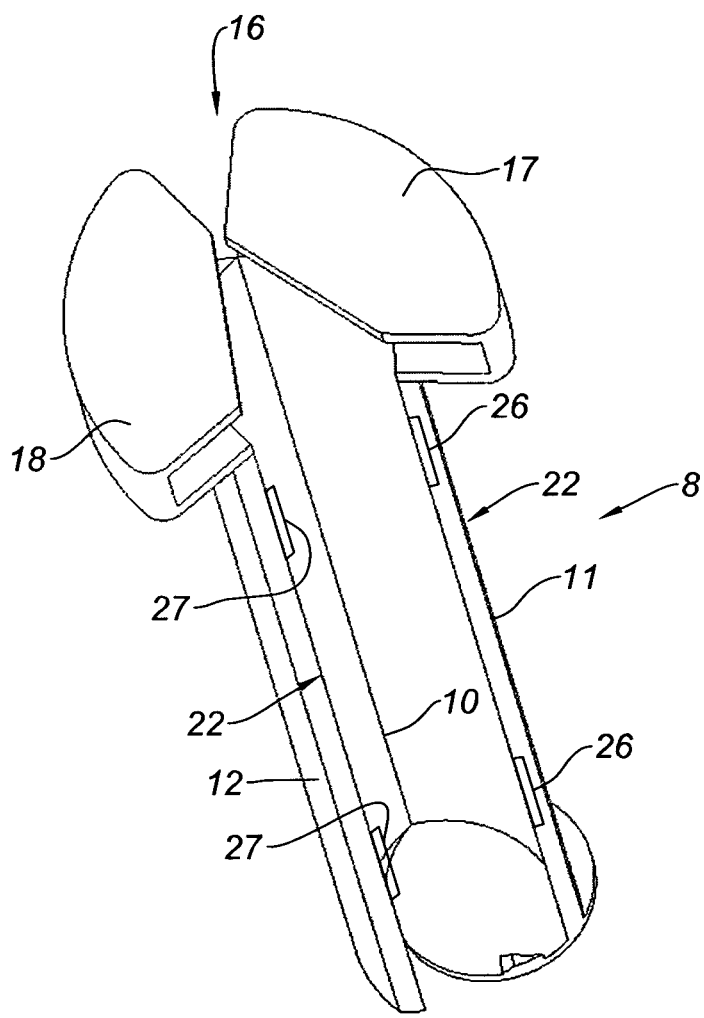

The present invention will now be described in greater detail with the aid of the following description and the appended drawings in which:

FIG. 1 represents a view in perspective of a drug delivery device of the invention in its packaged condition, FIG. 2 represents a view in perspective of the device of FIG. 1 in the position where a user has started releasing the connecting means between the plunger rod and the tray, FIG. 3 represents a view in perspective of the drug delivery device of FIG. 1 once the plunger rod has been separated from the tray, FIG. 4 represents a view in perspective of the plunger rod of the drug delivery device of FIG. 1, FIG. 5 represents a view in perspective of the drug delivery device of FIG. 1 in its use condition, FIG. 6 is a cross section and perspective view of the drug delivery device of FIG. 1 along plane II', FIG. 7 is a cross section view of the drug delivery device of FIG. 1 along plane II', FIG. 8 is view in perspective of the plunger rod of the drug delivery device of FIG. 1, FIG. 9 is a view in perspective of the tray of the package of FIG. 1 once the plunger rod has been removed therefrom, FIG. 10 is a view in perspective of an alternative embodiment of the packaged drug delivery device of FIG. 1, FIGS. 11 and 12 are views in perspective of respectively the upper part and the lower part of the package of FIG. 10, FIG. 13 is a view in perspective of two identical packages of the invention stacked up together, FIG. 14 is an exploded view of the stacked up packages of FIG. 13, FIG. 15 is a view in perspective of an alternative embodiment of the drug delivery device of the invention in its packaged condition, FIG. 16 is a cross section view of the packaged delivery device of FIG. 15, FIG. 17 is a view in perspective of another embodiment of the drug delivery device of the invention in its packaged condition, FIG. 18 is a cross section view of the packaged drug delivery device of FIG. 17, FIG. 19 is a view in perspective of the packaged drug delivery device of FIG. 17 once the tear-off line has been removed, FIG. 20 is a view in perspective of the tear-off line of embodiments of FIG. 15 and of FIG. 17, FIG. 21 is a cross section view of an alternative embodiment of the package of the invention, FIG. 22 is a perspective view of the plunger rod of the embodiment of FIG. 21.

With reference to FIGS. 1, 6 and 7 is shown a drug delivery device 1 of the invention in its storage condition, i.e. with its container 2 packaged in a package 3 of the invention. With reference to FIG. 3, the drug delivery device 1 comprises a container 2 comprising a tubular barrel 4, such as a syringe body, having a longitudinal axis A, having open distal and proximal ends, the proximal end being sized and shaped to receive a plunger 20 (see FIGS. 6 and 7), and the distal end being sized and shaped to receive an injection needle (not shown), which may be, for example, a staked needle. On the example shown, the tubular barrel 4 is provided at its proximal end with a flange 5. It is also provided with a cap 6 closing its distal end. In case the tubular barrel is provided at its distal end with a staked needle, the cap surrounds and protect said staked needle. The container 2 may be prefilled with a product, such as a drug or a medicine, to be delivered. In such a case, in addition to the cap 6 closing the distal end of the tubular barrel 4, the container 2 is further provided with a plunger 20 closing the proximal end of the tubular barrel 4 so as to prevent leakage of the product out of the tubular barrel 4.

With reference to FIGS. 1, 3, 6 and 7, the container 2 is received within a package 3, surrounding the container 2, and having a shape substantially matching that of the outer volume of the container 2 in the example shown. As a consequence, on the example shown, the package 3 has the same longitudinal axis A as the container 2. On the example shown, the package 3 has globally the shape of a tube provided at its proximal end with an outer flange 21, intended to receive the flange 5 of the tubular barrel 4, and at its distal end with a projecting screw 13, the function of which will be explained below.

As appears from FIGS. 1-3, the package 3 comprises a plunger rod 8 for said container 2, and a tray 9, connected to said plunger rod 8 on FIG. 1, said tray 9 and said plunger rod 8 forming said package 3 when they are connected to each other. The plunger rod 8 and the tray 9 are therefore complementary parts forming the package 3 surrounding the container 2. The tray 9 and the plunger rod 8 are connected to each other along a junction outline 22 delimiting the plunger rod 8 with respect to said tray 9.

The path of the outline 22 may be more clearly visible thanks to FIG. 9 showing the tray 9 of the package 3 on its own, said tray 9 having a periphery 19, the shape of which is complementary to the outline 22 delimiting the plunger rod 8. The tray 9, which corresponds to the part of the package 3 free from the plunger rod 8, may be made of any plastic material or polyolefin material and may have any rigidity: for example, the tray 9 may be made of a rigid shell or alternatively of a plastic film.

In the example shown on FIGS. 1-9, the tray 9 has a shape complementary to that of the plunger rod 8 so that, once connected to each other, the tray 9 and the plunger rod 8 form globally the tubular shape of the package 3. Anyway, the package 3 needs not necessarily have a globally outer tubular shape: as will appear in other embodiments below, the global outer shape of the package may be different from a tube, and may be rather rectangular for example. In such a case, the outer shape of the tray may also be different than tubular and may be rectangular or have any outer shape, as long as when connected to the plunger rod, it forms a package substantially surrounding and protecting the container.

As will appear from further description of FIG. 1-9 below, the plunger rod 8 and the tray 9 are connected to each other by releasable connecting means: these releasable means are for example located in the vicinity of the junction outline 22.

On the example shown on FIGS. 1-9, part of the releasable connecting means is located between the plunger rod 8 and the tray 9 and other part of the releasable connecting means is located on the plunger rod 8 and on the tray 9.

The part of the releasable connecting means that is located between the plunger rod 8 and the tray 9 is a tear-off line 7 located on a part of the junction outline 22: as appears from FIG. 2, the tear-off line 7 runs only on one side of the plunger rod 8 and it has a proximal end 7a and a distal end 7b. In the example shown, the part of the releasable connecting means which is located on the plunger rod 8 and on the tray 9 is snap-fit means for connecting the plunger rod 8 to the tray 9 in a region of the outline 22 free from any tear-off line. In the example shown, these snap-fit means are under the form of pegs 23 provided on the tray 9 of the package 3 and engaged into recesses 24 provided on the plunger rod 8 and are visible on FIG. 7. For example, the package 3 may be provided with two pairs of snap-fit means, i.e. peg and recess, axially spaced from each other on the side of the plunger rod 8 opposite the tear-off line 7. Once the tear-off line 7 has been completely torn off, the user can easily release the pegs 23 from the recesses 24 so that the plunger rod 8 and the tray 9 of the package 3 are totally separated from each other, as shown on FIG. 3.

FIG. 3 shows the drug delivery device 1 of FIG. 1 once the tear-off line 7 has been completely torn off and the snap-fit means (23, 24) released, thereby totally freeing the plunger rod 8 from the tray 9 of the package 3.

Moreover, tearing the tear-off line 7 and releasing the snap-fit means (23, 24) also results in opening the package 3 and gaining access to the container 2.

In another embodiment, which will be described with reference to FIGS. 21 and 22, the tear-off line 7 is replaced by additional snap-fit means.

The plunger rod 8 will now be described on its own with reference to FIGS. 3, 4 and 8 on which it is shown once having been freed from the package 3. The plunger rod 8 has a part shaped complementarily to a part of the external shape of the tubular barrel 4: this part has globally the shape of a longitudinal section of a tube and is provided with a longitudinal living hinge 10 separating this longitudinal section of a tube in two portions, a first longitudinal portion 11 and a second longitudinal portion 12, of similar size on the example shown. The material forming the plunger rod 8 is of sufficient rigidity so as to allow it to be used in combination with the container 2, for moving a plunger as will appear from the description below. Such a material may be selected from polyolefin materials such as polyethylene or polypropylene.

As appears from FIGS. 5 and 8, the longitudinal living hinge 10 allows the first longitudinal portion 11 and the second longitudinal portion 12 of the plunger rod 8 to be folded one onto the other.

The plunger rod 8 is provided at its distal end with attaching means, under the form of a projecting screw 13 on the example shown, for attaching said distal end to the plunger 20 present in the tubular barrel 4, said plunger 20 being provided with a threaded recess (not shown) matching the thread of the screw 13. On the example shown, the screw 13 extends distally from a transversal wall 14 provided at the distal end of the first longitudinal portion 11 (see FIG. 8). As part of the plunger rod 8, the projecting screw 13 is therefore part of the package 3 as appears from FIGS. 1 and 2. In embodiments not shown, the attaching means could be under the form of snap-fit means and they alternatively could be located on the second longitudinal portion 12. As appears also from FIGS. 4 and 8, the plunger rod 8 is further provided with clipping means, such as a peg 15, for clipping the first longitudinal portion 11 to the second longitudinal portion 12 in a folded position as shown on FIG. 5. On the example shown, the peg 15 is provided on the transversal wall 14 of the first longitudinal portion 11 and it is intended to be engaged within a complementary recess (not shown) located on the second longitudinal portion 12.

When the peg 15 is engaged in its complementary recess, the rigidity of the plunger rod 8 is reinforced by the presence of the double wall formed by the two longitudinal portions (11, 12) being locked in a folded configuration.

On the example shown, the plunger rod 8 is further provided at its proximal end with a partial flange 16, which corresponds to the part of the outer flange 21 of the package 3 which is aligned on the plunger rod 8. The partial flange 16 is made of two parts, a first part 17 integrated with the first longitudinal portion 11 of the plunger rod 8, and a second part 18, integrated with the second longitudinal portion 12 of the plunger rod 8. Each part (17, 18) is designed so as to be able to receive part of the flange 5 of the tubular barrel 4 in the packaged configuration of the drug delivery device of the invention, as shown on FIGS. 1 and 2. Once the first longitudinal portion 11 and the second longitudinal portion 12 of the plunger rod 8 are folded one onto the other and clipped together, as shown on FIG. 5, the two parts (17, 18) of the partial flange 16 form a reliable pushing surface for the user in order to perform the injection or delivery of the product.

In embodiments not shown, the peg 15 and its complementary recess could be located partly on the first part 17 and partly on the second part 18 of the partial flange 16.

With reference to FIG. 9 is shown the tray 9 of the package 3 once the plunger rod 8 has been removed from the package 3. This tray 9 is intended to receive and protect the container 2 in the packaged configuration of the drug delivery device 1 as shown on FIG. 1. As such, the inner shape of the tray 9 is preferably complementary to the external shape of the container 2, as shown on this Figure. As seen above, the outer shape of the tray 9 may be any shape, for example mostly tubular as shown on FIG. 9, or on the contrary rectangular, as shown on FIGS. 15 and 17.

Preferably, in general, the outer shape of the tray of the package of the invention is such that the tray is easily stackable with another same shaped tray.

Once the package 3 has been opened and once the container 2 and the plunger rod 8 have been removed in order to reconstitute the drug delivery device 1 of the invention, the tray 9 may be discarded. The periphery 19 of the tray 9 is complementary to the junction outline 22 defining the plunger rod 8.

The tray 9 may be of any material capable of taking the desired shape for forming a package, complementarily with the plunger rod. Such a material may be selected from polyolefins, such as polyethylene, polypropylene. When the package 3 of the invention comprises at least a tear-off line 7 located between the plunger rod 8 and the tray 9 as at least part of the releasable connecting means, the plunger rod 8 and the tray 9 may be made of thermoplastic materials that are co-injected in a molding process.

The reconstitution of the drug delivery device of the invention from its packaged configuration in the package of the invention will now be explained with reference to FIGS. 1 to 9.

The user is provided with the drug delivery device 1 of FIG. 1 in the packaged condition of the container 2. In the explanation below, one assumes that the container 2 is prefilled with a product to be delivered and closed with a cap without any needle.

As appears clearly from FIGS. 6 and 7, in the packaged configuration of the container of the drug delivery device 1 of the invention, the part of the plunger rod 8 that is shaped complementarily to a part of the external shape of the tubular barrel 4 is in a nesting relationship with said tubular barrel 4. As a consequence, no space is wasted between the tubular barrel 4 and the plunger rod 8. Moreover, because, in this example, this part of the plunger rod 8 is a longitudinal section of a tube, the combination of the tubular barrel 4 and the plunger rod 8 occupies as little space as possible. The packaged drug delivery device 1 of the invention is therefore very compact and fills as little space as possible.

The user grasps the packaged drug delivery device 1 of FIG. 1 and he tears off the tear-off line 7 as shown on FIG. 2. Once the tear-off line 7 has been completely torn off on one side of the junction outline 22, the user releases the snap-fit means connecting the rest of the plunger rod 8 to the tray 9 by disengaging the pegs 23 from the recesses 24 on the opposite side of the outline 22. In the example shown, no additional connecting means are provided at the proximal end of the package 3, i.e. in the flange 21 area, or at its distal end, i.e. in the screw 13 area. As a consequence, the plunger rod 8 is now totally separated from the tray 9 and the user has access to the prefilled container 2, as shown on FIG. 3. The user then removes the prefilled container 2 from the tray 9 which is discarded. The user then folds the first longitudinal portion 11 of the plunger rod 8 onto its second longitudinal portion 12 and he clips the two longitudinal portions together by engaging the peg 15 in a complementary recess (not shown), as shown on FIGS. 4 and 5, thereby constituting a rigid rod capable of being used in combination with the prefilled container 2 to move the plunger 20 (see FIG. 7) present in the prefilled container 2, in particular after having attached the screw 13 of the plunger rod 8 to the plunger 20, as shown on FIG. 5.

In other embodiments not shown, the plunger rod is not provided with attaching means and needs not be attached to the plunger. For example, the distal end of the plunger rod may simply contact the plunger and push it distally upon pressure exerted by the user.

The user needs only remove the cap 6 from the distal end of the prefilled container 2 and connect a needle thereon to be in possession of an injection device ready to be used.

As appears from the description above, in its packaged condition, the drug delivery device 1 of the invention is very compact and requires only little space during storage. This is particularly advantageous for hospitals and pharmacies where a large number of injection devices, in particular prefilled devices, need to be stored.

With reference to FIGS. 10-12 is shown an alternative embodiment of the package of embodiment of FIGS. 1-9, in which the package comprises means for stacking up the packaged drug delivery device with another identical packaged drug delivery device, so that the two stacked up packaged drug delivery devices occupy as little space as possible.

On FIG. 10 is shown a package 103 suitable for use with a container 2 as shown on FIGS. 1-9. The package 103 comprises a plunger rod 108 and a tray 109, said plunger rod 108 being delimited with respect to said tray 109 by an outline 122, a part of which is formed by a tear-off line 107 having a proximal end 107a and a distal end 107b. With reference to FIGS. 11-12, the package 103 is made of a first shell 110 and a second shell 111, each having globally a semi-tubular shape and being complementary to the other, thereby forming the package 103 when they are clipped one onto the other by means of snap-fit means 113: the snap-fit means 113 include pegs 114 located on the first shell 110 and recesses 115 located on the second shell 111, the pegs 114 being engaged in the recesses 115 when the package 103 covers the container 2 so as to form a packaged container 2, in a similar way as in FIGS. 1-9.

In such an embodiment, where the package is made of two shells to be clipped together, the two shells are preferably made of a material having enough rigidity to allow clipping them together and to protect efficiently the barrel of the container to be packaged. Such a material may be selected from polyolefin materials such as polyethylene or polypropylene, or any plastic materials.

As appears from these Figures, the first shell 110 includes the plunger rod 108, the outline 122 being entirely located on the first shell 110.

As appears from these figures, the package 103 comprises a tubular part, made of the semi-tubular part of the first shell 110 and the semi-tubular part of the second shell 111. With reference to FIGS. 10-12, the second shell 111 is provided with a distal transversal wall 116: the distal transversal wall 116 has a first concave shape 116a, directed toward the first shell 110 when said first shell 110 is clipped on said second shell 111 and intended to engage the basis of the projecting screw 112 located at the distal end of the first shell 110. The distal transversal wall 116 has a second concave shape 116b, which is semi-circular and opposite said first concave shape 116a. The second concave 116b shape extends outwardly from said package 103 and is complementary to the outer circular convex shape of the semi-tubular part of the second shell 111.

This allows the tubular part of the second shell 111 to be engaged with the corresponding second concave shape 116b of a package 103 of another identical packaged container 2, as shown on FIGS. 13 and 14. On these Figures, the references designating the same elements as in FIGS. 10-12 have been maintained.

FIGS. 15 to 20 show alternative embodiments of the package of the invention, in which the plunger rod includes a solid shaft. The references designating the same elements as in FIGS. 1-9 have been maintained.

With reference to FIGS. 15 and 16 is shown a packaged drug delivery device 201 comprising a container 2 and a package 203: the package 203 is formed of a plunger rod 208 and a tray 209 connected to each other by a tear-off line 207 running along the entire length of a junction outline 222 delimiting the plunger rod 208 with respect to the tray 209. In this embodiment thus, the releasable connecting means for connecting the plunger rod 208 to the tray 209 consists in one single removable tear-off line 207. An example of such a tear-off line, represented on its own once it has been removed, is shown on FIG. 20.

The plunger rod 208 is provided at its distal end with a projection screw 213 and at its proximal end with an outer flange 216. As appears from FIGS. 15 and 16, the plunger rod 208 includes a solid shaft 210 linking together the proximal end, i.e. the outer flange 216, and the distal end, i.e. the projecting screw 213, of said plunger rod 208. In the present embodiment, the solid shaft 210 is the part of the plunger rod 208 shaped complementarily to at least a part of the external shape of the tubular barrel 4: indeed, as clearly appears from FIG. 16, the solid shaft 210 shows a concave longitudinal face 210a which is in a nesting relationship with the external wall of the tubular barrel 4 in the packaged configuration of the drug delivery device 201. As is clear from FIG. 16, in such a configuration, no space is wasted between the tubular barrel 4 and the plunger rod 208 and the combination of the tubular barrel 4 and the plunger rod 208 occupies as little space as possible.

The solid shaft 210 is preferably made of a rigid material as described above, for example polyolefin materials such as polyethylene or polypropylene. Such a packaged drug delivery device 201 may be used as described above for embodiment of FIGS. 1-9. Nevertheless, with the embodiment of FIGS. 15-16, the user needs not reconstitute a plunger rod by folding on themselves two portions of the plunger rod: as it appears from these Figures, once the tear-off line 207 has been completely removed from the package 203, the plunger rod 208 is readily available, thanks to the presence of the solid shaft 210.

As appears from FIG. 16, the inner shape of the tray 209 is complementary to the part of the outer shape of the tubular barrel 4 which is not facing the rigid shaft 210. The outer shape of the tray 209 is partly rectangular. The package 203 is therefore easy to stack up with other such packages 203.

With reference to FIGS. 17-20 is shown an alternative embodiment of FIGS. 15-16, where the path of the tear-off line is different and requires the container 2 to be pulled off from the tray after removal of said tear-off line.

With reference to FIGS. 17-20 is shown a packaged drug delivery device 301 comprising a container 2 and a package 303 : the package 303 is formed of a plunger rod 308 and a tray 309 connected to each other by a tear-off line 307 running along the entire length of junction outline 322 delimiting the plunger rod 308 with respect to the tray 309. In this embodiment thus, the releasable connecting means for connecting the plunger rod 308 to the tray 309 consists in one single removable tear-off line 307. The tear-off line 307 is shown on FIG. 20 once it has been completely removed from the package 303. The plunger rod 308 is provided at its distal end with a projection screw 313 and at its proximal end with an outer flange 316. As appears from FIGS. 17-20, the plunger rod 308 includes a solid shaft 310 linking together the proximal end, ie the outer flange 316, and the distal end, ie the projecting screw 313, of said plunger rod 308. In the present embodiment, the solid shaft 310 is the part of the plunger rod 308 shaped complementarily to at least a part of the external shape of the tubular barrel 4: indeed, as clearly appears from FIG. 18, the solid shaft 310 shows a concave longitudinal face 310a which is in a nesting relationship with the external wall of the tubular barrel 4 in the packaged configuration of the drug delivery device 301. As is clear from FIG. 18, in such a configuration, no space is wasted between the tubular barrel 4 and the plunger rod 308 and the combination of the tubular barrel 4 and the plunger rod 308 occupies as little space as possible.

The solid shaft 310 is preferably made of a rigid material as described above. Such a packaged container may be used as described above for embodiment of FIGS. 1-9. Nevertheless, with the embodiment of FIGS. 17-20, like for embodiment of FIGS. 15-16, the user needs not reconstitute a plunger rod by folding on themselves two portions of the plunger rod: as appears from FIGS. 18 and 19, once the tear-off line 307 has been completely removed from the package 303, the plunger rod 308 is readily available, thanks to the presence of the solid shaft 310. As appears also from FIG. 19, once the tear-off line 307 has been removed, the user may pull off the container 2 from the tray 309 in order to remove the container 2 from the package 303.

As appears from FIG. 18, the inner shape of the tray 309 is complementary to the part of the outer shape of the tubular barrel 4 which is not facing the rigid shaft 210. The outer shape of the tray 209 is partly a square. The package 303 is therefore easy to stack up with other such packages 303.

With reference to FIGS. 21 and 22 is described a package 3 similar to that of FIGS. 1-9 but where the tear-off line 7 is replaced by snap-fit means under the form of a peg 27 provided on the plunger rod 8 and a recess 28 provided on the tray 9, said peg 27 and recess 28 cooperating together so as to connect the plunger rod 8 to the tray 9. Moreover, the peg 24 and recess 23 of embodiment of FIGS. 1-9 are replaced by a peg 25 provided on the tray 9 and a recess 26, provided on the plunger rod 8, said peg 25 and recess 26 further cooperating together, in addition to peg 27 and recess 28, so as to connect the plunger rod 8 to the tray 9, as shown on FIG. 21.

Moreover, recess 26 and peg 27, both provided on the plunger rod 8, are shaped complementarily, so that when the plunger rod 8 is no more connected to the tray 9, as shown on FIG. 22, then the peg 27 is capable of cooperating with recess 26 so that the first longitudinal portion 11 and the second longitudinal portion 12 of the plunger rod 8 may be clipped together in order to maintain them folded one on the other in a locked configuration.

The package of the invention allows to reduce drastically the volume occupied by the drug delivery device during storage, in particular when the container of the drug delivery device is prefilled with a medicine: indeed, the length necessary for storing the plunger rod of devices of the prior art is not necessary in the present invention, where the plunger rod is reconstituted from or is part from the package. Moreover, the packaged drug delivery devices of the invention can be stacked up together so as to gain space for storage.

The invention claimed is:

1. A package for a container comprising:
   a tubular barrel having open distal and proximal ends, the proximal end being sized and shaped to receive a plunger, and the distal end configured to receive an injection needle, said package comprising:
   i) a plunger rod for said container, a part of said plunger rod being shaped complementarily to at least a part of the external shape of said tubular barrel, and
   ii) a tray connectable to said plunger rod, said tray and said plunger rod forming said package when they are connected to each other, wherein said package at least partially encloses said tubular barrel, wherein the part of the plunger rod comprising a first longitudinal portion and a second longitudinal portion, wherein at least a first member of a lock is located on said first longitudinal portion and a second member of a lock is located on said second longitudinal portion, and wherein said first and second members are engageable with each other when said plunger rod is not connected to the tray.

2. A package according to claim 1, wherein said plunger rod and said tray are connected to each other by a releasable connecting member.

3. A package according to claim 2, wherein at least part of said releasable connecting member is provided between said plunger rod and said tray.

4. A package according to claim 2, wherein at least part of said releasable connecting member is provided on said plunger rod and on said tray.

5. A package according to claim 2, wherein said releasable connecting member comprises a lock.

6. A package according to claim 2, wherein at least part of said releasable connecting member is provided on one of said plunger rod and tray.

7. A package according to claim 3, wherein said releasable connecting member comprises one removable tear-off line delimiting the outline of said plunger rod with respect to said tray.

8. A package according to claim 1, wherein the first longitudinal portion and the second longitudinal portion are coupled to each other by a longitudinal living hinge.

9. A package according to claim 1, wherein the part of the plunger rod that is shaped complementarily to at least a part of the external shape of the tubular barrel is a solid shaft showing at least one concave longitudinal face.

10. A package according to claim 1, wherein the plunger rod includes a first end for attaching said plunger rod with the plunger intended to be received in said container.

11. A package according to claim 1, wherein the plunger rod is attachable with the plunger at a distal end of one of said first longitudinal portion and said second longitudinal portion.

12. A package according to claim 9, wherein the plunger rod is attachable with the plunger at a distal end of said solid shaft.

13. A package according to claim 1, wherein a flange is provided at a proximal end of said plunger rod.

14. A package according to claim 1, wherein said tray comprises an outer shape for stacking engagement with another said tray.

15. A package according to claim 5, wherein the lock comprises a peg extending from the tray and a recess formed in the plunger rod, the recess sized to receive the peg, the peg removably connectable with the recess.

16. A package according to claim 5, wherein the lock comprises a peg extending from the plunger rod and a recess formed in the tray, the recess sized to receive the peg, the peg removably connectable with the recess.

17. A package according to claim 1, wherein the first member of the lock comprises a peg and the second member of the lock comprises a recess, the recess sized to receive the peg, the peg removably connectable with the recess.

18. A package according to claim 14, wherein the outer shape of the tray includes a distal wall having a concave shape extending outwardly from the package and a proximal wall having an outer circular convex shape, the concave shape complementary to the outer circular convex shape of the proximal wall thereby allowing stacking engagement with another said tray.

* * * * *